United States Patent [19]

Broerman

[11] 4,276,907
[45] Jul. 7, 1981

[54] FLUID ACTUATED VALVE

[75] Inventor: Arthur B. Broerman, Bartlesville, Okla.

[73] Assignee: Phillips Petroleum Company, Bartlesville, Okla.

[21] Appl. No.: 96,716

[22] Filed: Nov. 21, 1979

[51] Int. Cl.³ ............... F16K 31/143; F16K 31/163; F16K 31/363
[52] U.S. Cl. ................................ 137/637.2; 251/62
[58] Field of Search ............. 73/422 GC; 251/62, 63, 251/331; 137/637.2

[56] References Cited

U.S. PATENT DOCUMENTS

| | | |
|---|---|---|
| 3,111,849 | 11/1963 | Broerman . |
| 3,139,755 | 7/1964 | Reinecke . |
| 3,140,615 | 7/1964 | Broerman . |
| 3,376,894 | 4/1968 | Broerman . |
| 3,387,496 | 6/1968 | Broerman . |
| 3,439,542 | 4/1969 | McRay . |
| 3,535,939 | 10/1970 | Casey et al. . |
| 3,545,491 | 12/1970 | Broerman . |
| 3,633,426 | 1/1972 | Broerman . |
| 4,112,766 | 9/1978 | Raigains . |

Primary Examiner—S. Clement Swisher

[57] ABSTRACT

A multi-part diaphragm-sealed valve suitable for use in high or low pressure chromatography of the type actuated by a spring biased within a cylinder. The piston is provided with a stop means to limit compression of the springs. A groove is provided in the cylinder wall to allow quick pressure build up and decay within the spring to insure quick action of the valve itself.

16 Claims, 10 Drawing Figures

FLUID ACTUATED VALVE

This invention relates to a multi-port diaphragm-sealed valve. In another aspect this invention relates to a fluid actuated, multipiston operated valve having utility as a sampling valve in both liquid chromatography and gas chromatography.

It is common practice to analyze fluid mixtures by means of chromatography. In a conventional chromatographic analyzer, a sample of the material to be analyzed is introduced into a chromatographic column, and carrier gas is thereafter passed through the column to elute the constituents of the sample in sequence. In order to obtain reproducible results, it is important that the sample volumes introduced into the column remain constant. This can be accomplished by means of sample valves which trap a predetermined volume of the sample in a loop and deliver this trapped volume to the column when the valve is actuated. A number of pneumatically operated diaphragm valves have been designed which are particularly effective for this purpose. Examples of some such valves are disclosed in U.S. Pat. Nos. 3,140,615; 3,376,894; 3,387,496 and 3,545,491, the disclosures of which are incorporated herein by reference.

While the valves illustrated in those patents operate in a satisfactory manner as sample valves in many chromatography processes, the advent of high pressure gas and liquid chromatography has created the need for valves which can function more reliably and accurately at the higher fluid pressures encountered in that type of chromatography.

One valve that was developed to meet this requirement is disclosed in U.S. Pat. No. 4,112,766, the disclosure of which is also incorporated herein by reference. The specifically illustrated valve in that patent includes upper and lower actuating pistons in sealing engagement with a casing, a bottom sealing the casing, a plunger housing at the top of the casing containing a plurality of passages through which plungers can travel, and a cap having a plurality of ports therethrough and a plurality of recesses on the bottom thereof. The upper and lower pistons have configuration such that when they are in one position a first half of the plungers press a cushion supported diaphragm against the lower face of the cap in such a fashion as to prohibit flow of fluid between the two ports adjacent each of said first half of said plungers. The other half of the plungers are maintained in a position removed from the lower surface of the cap so as to provide a path for a fluid under pressure to flow between the two ports adjacent each of said second half of said plungers. When the pistons change to the second position, the first half of the plungers drop away from the lower surface of the cap and the second half of the plungers move upward to press the diaphragm against the lower face of the cap to reverse the ports through which fluid can flow. The pistons are held in one of two possible positions as a result of the spring force provided by a plurality of alternately stacked Belleville spring washers positioned beneath the lowermost piston.

During the operation of valves of this type using the higher levels of actuating pressure, it has been noted that downward travel of the lower piston beyond the desired level can result in "snap-over" of some of the Belleville washers. When snap-over of Belleville washers occurs, it alters the operation of the valve so as to have adverse affects upon most chromatographic analyses. Accordingly, such snap-overs generally require interruption of the analyses so that the valve can be disassembled for replacement or realignment of the spring washers.

It has also been noted that in operation of such a valve, the Belleville washers when compressed tend to form a seal between themselves and other surfaces with which they are in contact. The seals formed by the Belleville washers result in a reduction in the speed with which pressure can buildup and decay in the chamber below the lower piston. Means for overcoming the sealing of the washers would improve the efficiency of the valves by permitting them to be switched more quickly and easily.

It has also been noted that in valves of the type illustrated in U.S. Pat No. 4,112,766, high pressure operation tends to result in extruding of the diaphragm into the recesses provided in the base of the cap. The extrusion of the diaphragm into the recesses in turn results in restriction or stoppage in the flow of fluid between the associated ports.

By various aspects of this invention, one or more of the following, or other, objects can be obtained.

One object of the present invention is to provide a new and improved multi-port, diaphragm-sealed valve suitable for use in high pressure chromatography as well as low pressure chromatography.

Another object of the present invention is to provide a means for limiting the distance of travel of the lower activating piston in order to provide a valve which may be more quickly switched from one position to another.

Still another object of the present invention is to provide means that will prevent snap-over of the Belleville washers.

Yet another object of the present invention is to provide a multi-port diaphragm-sealed valve in which there is less likelihood of diaphragm extrusion causing blockage of the valve ports.

Another object of this invention is to provide a valve in which pressure can buildup and decay quickly in the chamber beneath the lower operating piston.

Other aspects, objects, and the several advantages of this invention will be apparent to one skilled in the art from a study of this disclosure, the drawings, and the appended claims.

In the drawings,

FIG. 4 is a top plan view of a partially assembled valve of the type illustrated in FIGS. 2, 3 and 3a.

Figure 1:
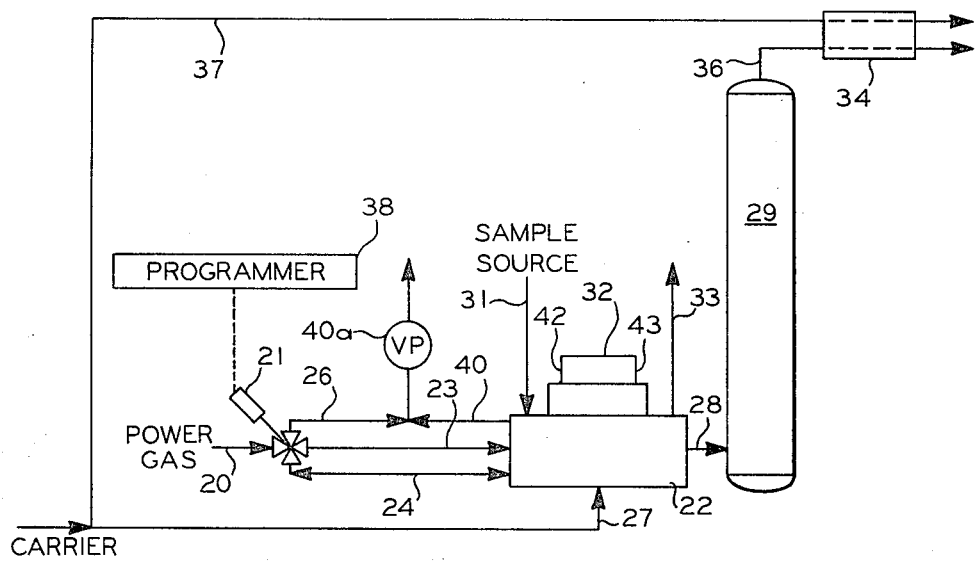
FIG. 1 is a schematic representation of a chromatographic analysis system in which the present inventive valve can be employed.
Figure 5:
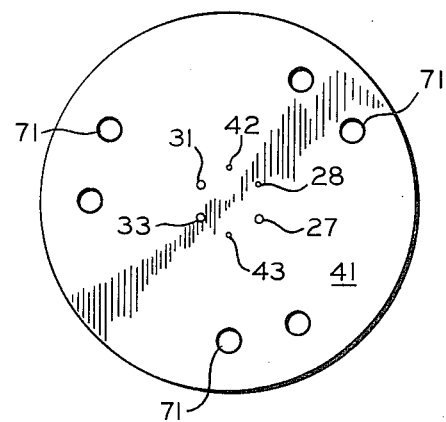
FIG. 5 is a bottom plan view of the upper member of the valve of FIG. 2.

Referring now to the drawings, wherein like parts have been designated by like reference numerals, and to FIG. 1 in particular, wherein a power gas, such as air, passes via conduit 20 to pilot valve 21, wherein the power gas stream is directed to a first chamber (not shown) of a pneumatically-actuated, diaphragm-sealed, sampling valve 22 via conduit 23 during a first time interval. Also, a second chamber (not shown) is vented through line 24, valve 21 and line 26. Vacuum pump 40a pulls a vacuum on line 26 as well as line 40 which draws a vacuum on a third chamber (not shown) which chamber is in communication with the underside of the sealing diaphragm to pull a continuous vacuum thereon as will be hereinafter described. In a second interval of time, the sampling valve 22 is vented via conduit 23, pilot valve 21, and pilot exhaust conduit 26. During this second interval of time, power gas passes through line 20, pilot valve 21, and conduit 24 to supply pressure to the second chamber. Valve 21 can be any suitable four-way valve or can be a combination of two or more three-way valves as will be hereinafter described with reference to FIGS. 5 and 6. A carrier gas, such as helium or hydrogen, is passed via conduit 27, sampling valve 22, and conduit 28 to column 29. A sample source (not shown) such as from process stream, is connected to sampling valve 22 via conduit 31, being circulated through sample loop 32 of sampling valve 22, and vented therefrom via sample exhaust conduit 33. Periodically, the sample in loop 32 is passed along with the carrier gas, via conduit 28, to sorption column 29, where constituents of the sample are absorbed or adsorbed, depending upon the nature of the contact material, and then are selectively desorbed by a continuing flow of carrier gas therethrough to be identified and measured.

The effluent from the sorption column 29 passes through an analyzer, indicated as thermal conductivity assembly 34, via conduit 36. The output signal from the detector 34 is passed to a recording instrument (not shown), which can be a conventional strip chart recorder. A stream of carrier gas is passed via conduit 37 from conduit 27 directly to the reference cell of detector 34, so as to balance out the effect of the carrier gas in the column 29 effluent. The sample gas to be analyzed generally enters the system continuously through conduit 31. It is exhausted through conduit 33, even when a slug thereof is selected for analysis. Pilot valve 21 is actuated by programmer 38, which can be operated by a time cycle or other means.

When pilot valve 21 is changed from the first described position, power gas is now exhausted from sampling valve 22 via conduit 23. Carrier gas now passes to sample loop 32, collecting the sample trapped therein, and carrying the same to sorption column 29, via conduit 28. Thus, each time power gas is supplied to conduit 24 and gas is exhausted from conduit 23 through valve 21 and line 26, a measured sample is passed via conduit 28 to column 29 for sorption and desorption therein. The carrier gas carries the measured sample, as determined by the loop size, into the column.

Figure 2:
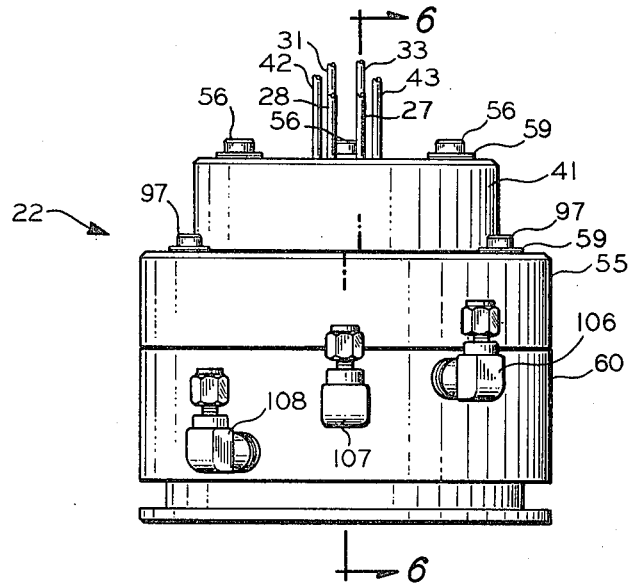
FIG. 2 is an elevational view of an assembled fluid-actuated multi-piston operated valve falling within the scope of the present invention.

In FIG. 2, there is shown an elevation view of an assembled valve of this invention, generally designated 22. The valve 22 comprises an upper cap 41 provided with six small diameter conduits 27, 28, 31, 33, 42, and 43, which communicate directly with the lower surface of the upper cap by spaced vertical passages 48 to 52 some of which can be seen more clearly in FIG. 6. Conduits 42 and 43 can be connected to provide a sample loop 32. Adjacent the upper cap there is a plunger housing 55 to be described in more detail shortly. Allen head screws 56 secure cap 41 to plunger housing 55. Beneath plunger housing 55 there is a piston housing 60. Allen head screws 97 secure the plunger housing 55 to the piston housing 60. Plural Belleville washers, such as 59, are positioned on the shaft of each of the Allen head screws. Washers 59 permit the various parts to be tightened down evenly. This is due to the feel of slowly increasing torque as the washers flatten, indicating when further tightening could damage some of the valve parts. While it is not absolutely necessary to employ the Belleville washers 59 in combination with the cap screws, it is preferable.

Piston housing 60 is provided with threaded passages 61, 62, and 64. Conventional off-the-shelf pipe-to-tube fittings 106, 107, and 108 are secured in respective ones of those threaded passages.

Figures 3, 3A:
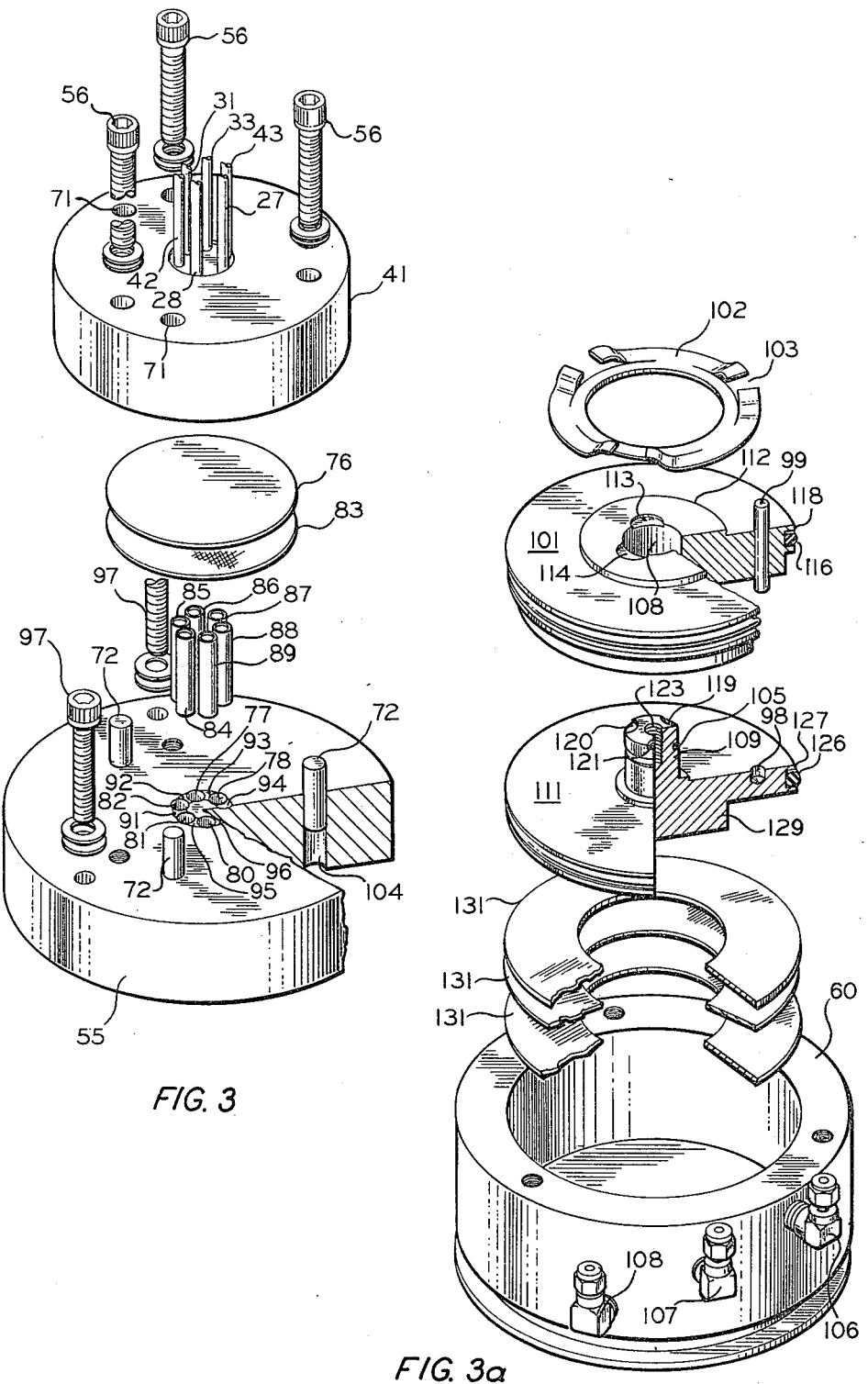
FIGS. 3 and 3a are exploded perspective views of the components of the valve shown in FIG. 2 arranged in the order of their assembly.
Figure 6:
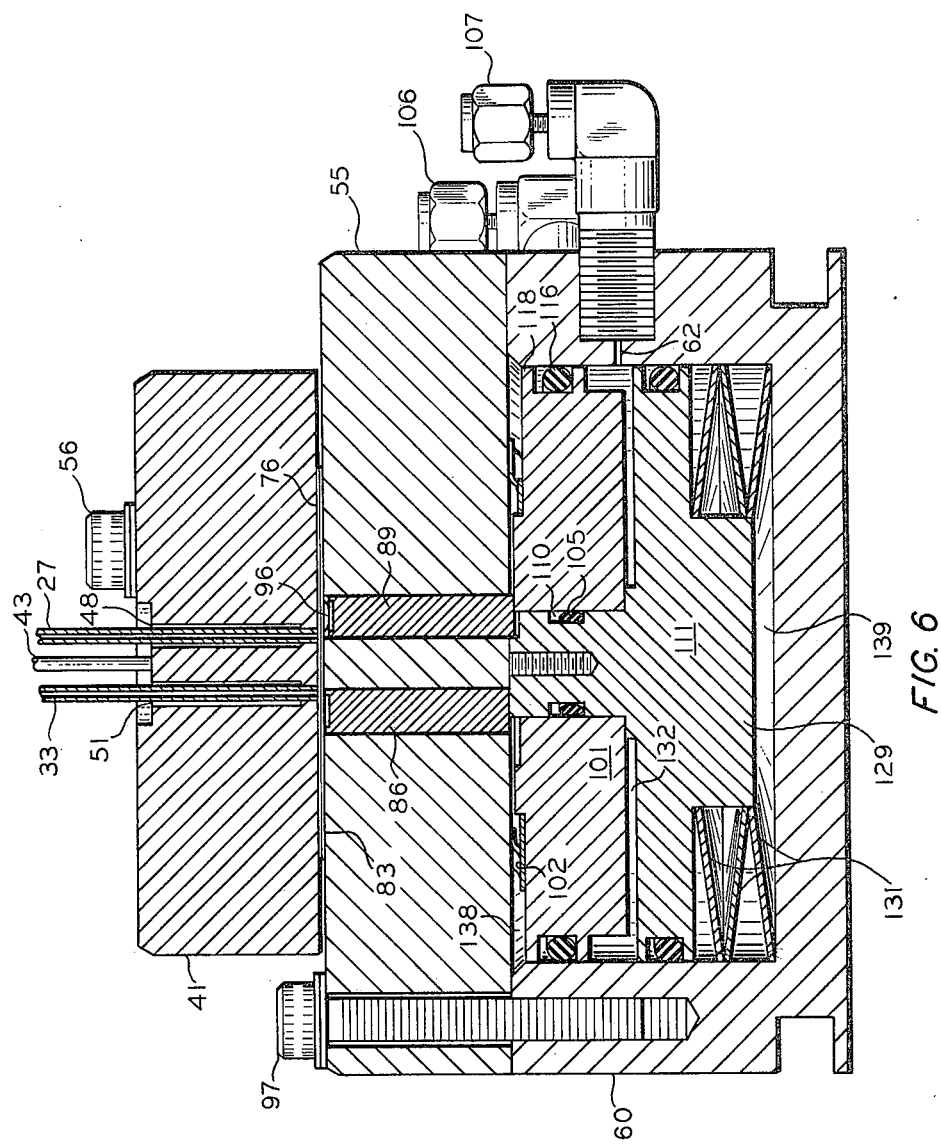
FIG. 6 is a sectional view of the valve of FIG. 2 as taken through line 6—6 of FIG. 2.

A more detailed illustration of the valve is provided by FIGS. 3, 3a and 6. Disposed intermediate the cap 41 and the plunger housing 55 are a flexible sealing diaphragm 76, and a cushion 83.

The sealing diaphragm 76 is preferably composed of a thermosetting plastic which is chemically inert and heat resistant, such as Teflon (a polymer of tetrafluoroethylene). The diaphragm can be of any suitable thickness. A thickness of about 4 mil is currently preferred.

The cushion 83 serves to prevent the diaphragm from cold flowing and also furnishes support for it to prevent ballooning under alternating carrier and power gas pressure, which results in an extended cycling life for the valve. Cushion 83 also serves to distribute pressure on the flexible diaphragm against the lower face of the cap, thus evening out any variations in the thickness of the diaphragm. The cushion can be of any suitable material and thickness. Presently a 2 mil thick cloth of Dacron (a polyester fiber) is preferred. The cushion 83 is at least as large in diameter as the diaphragm 76. Preferably, the diaphragm and the cushion 83 are of the same diameter.

The plunger housing 55 contains vertical cylindrical passages 77 to 82 extending therethrough. The upper surface of the plunger housing includes pins 72 that align cap 41 properly relative to housing 55 by fitting into vertical passages 71 that extend through the cap 41. When the housing and the cap are so properly assembled, each of the ports of conduits 27, 28, 31, 33, 42 and 43 will be positioned directly above but between respective pairs of vertical passages 77 to 82. Preferably, the pins 72 are placed, as illustrated, in a circle having a diameter such that the pins can contact the outer edge of the cushion 83 and the diaphragm 76 so as to assure centering of those components.

The plunger housing further includes curved recesses 91 to 96, about 0.010 to about 0.014 inch in depth, extending from one of said vertical passages to another within the circle described by the outer and innermost portions of the vertical passages 77 to 82.

A set of metal plunger rods 84 to 89 are provided for being positioned in respective ones of passages 77 to 82. The rods are machined to have a central relief in their upper end which provides an annular-shaped contact surface that allows more sealing per unit area to be exerted against the adjacent areas of cushion 83, in the operation as will be described shortly. The lower end of each rod is rounded to eliminate peening thereof with extended operation of the valve. Such peening would otherwise result in malfunctioning of the rods which would further result in shortening the life of the valve. The rods are all of equal length. It is possible, though less desirable, to replace the rods by a series of spheres surmounted by a hemisphere having a flat surface thereof facing the lower surface of cap 41 as in Broerman, U.S. Pat. No. 3,376,894, or any other suitable plunger means.

The diaphragm 76 has a diameter sufficiently large to completely cover the passageways 77 to 82 and the recesses 91 to 96. Preferably the diameter of the diaphragm is about two times the diameter of the circle defined by the outer surface of said passageways and recesses. This larger diameter allows for more even distribution of force when the cap is tightened to the body. The distribution of force over a larger area also diminishes the possibility of having the pressure cause extrusion of the diaphragm into the ports of conduits 27, 28, 31, 33, 42, and 43.

A crimped metal retracting spring 102 machined from spring steel stock is provided for being disposed between the lower surface of the plunger housing 55 and the upper surface of piston 101. The cut outs, such as 103, are aligned to permit the passage of alignment pin 99 to anchor in one of three recesses 104 provided in the lower surface of plunger housing 55. The recesses 104 are positioned directly beneath alignment pins 72. The recesses 104 are of such depth as to permit pin 99 to move longitudinally therein when the valve is switched from one position to another.

The upper most surface of piston 101 is provided with an annular shoulder 112 and push member for rods 85, 87, and 89. Shoulder 112 is provided with three notched out recesses 113 to 115 which are adapted to receive the lower ends of plunger rods, 84, 86, and 88. The recesses 113–115 are of a depth such that when piston 101 is moved upward to push plungers 85, 87, and 89 into sealing engagement with diaphragm 76, the plungers 84, 86, and 88 will be dropped sufficiently so as not to be in sealing engagement with diaphragm 76. In a preferred embodiment, the recesses 113–115 have a depth of about 0.01° inch. A resilient O-ring seal 116 is provided in a slot 118 in the periphery of piston 101, permitting sealing contact with the inner wall of the piston housing 60. The outer periphery of the cylindrical shoulder 112 has a diameter such as to act as a retainer for spring 102. Guide pin 99 extends completely through piston 101. A passage 108 extends centrally through the piston 101.

Piston 111 has a central projecting section 109 on its upper surface capable of extending upwardly through passage 108 of piston 101. An O-ring seal 105 is provided in a groove 110 in section 109 for permitting sealing contact with the inner wall of passageway 108. Another O-ring seal 126 is provided in a groove 127 in the outermost periphery of piston 111 permitting sealing contact with the inner wall of piston housing 60. The upper surface of projection 109 includes three spaced apart recesses, 119 to 121 and a central threaded recess 123. Threaded recess 123 is provided so that a screw or the like can be attached there to enable one to pull the pistons out of the piston housing for disassembly. Recesses 119 to 121 are of a depth sufficient to assure that when piston 111 forces plunger 84, 86, and 88 into sealing engagement with the diaphragm plungers 85, 87, and 89 will be dropped so as not to be in sealing engagement with the diaphragm. Preferably recesses 119 to 121 are about 0.010 inch in depth.

Figure 4:
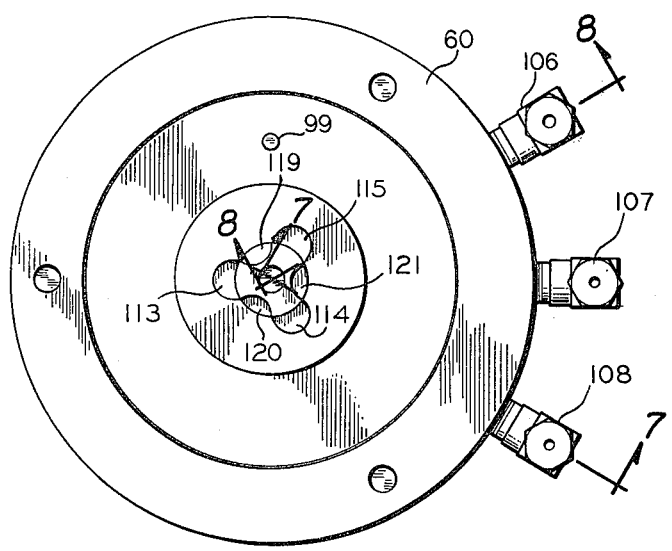

The upper surface of piston 111 further includes a recess 98. The recess 98 of piston 111 and the pin 99 of piston 101 are so positioned such that when pistons 101 and 111 are assembled with pin 99 in recess 98, the recesses 119 to 121 of the piston 111 are positioned between the recesses 113 to 115 of piston 101. This is most clearly illustrated in FIG. 4.

The bottom surface of piston 111 is provided with a central downwardly projected section 129, which can extend down through Belleville washers, such as 131, which are grouped in an opposing relationship to give the desired amount of upward bias as will be described shortly. The projection 129 extends downwardly a sufficient distance to insure that none of the Belleville washers will "snap-over" when fluid pressure is applied above piston 111. The projection 129 further serves to limit the downward movement of piston 111. Thus the projection 129 serves also as an over-travel stop which shortens the response time required for switching the valve.

It is generally preferred for the Belleville washers 131 to be stronger than spring 102. Other arrangements are possible but require much more complicated control of the valve actuating fluids.

In FIG. 6, there is shown in full section, except for the assembly screws, the valve in the "at rest" assembled state, i.e., with "no" actuating air being applied. In the assembled "at rest" state, the diaphragm 76 and the cushion 83 are clamped between the cap 41 and the plunger housing 55 by screws 56 to 58. The plunger housing is in turn secured in metal-to-metal sealing engagement with the piston housing 60. Although it is presently not considered necessary, one could, if circumstances warranted it, employ O-ring seals between the cap and the plunger housing and the plunger housing and the piston housing.

Figure 7:
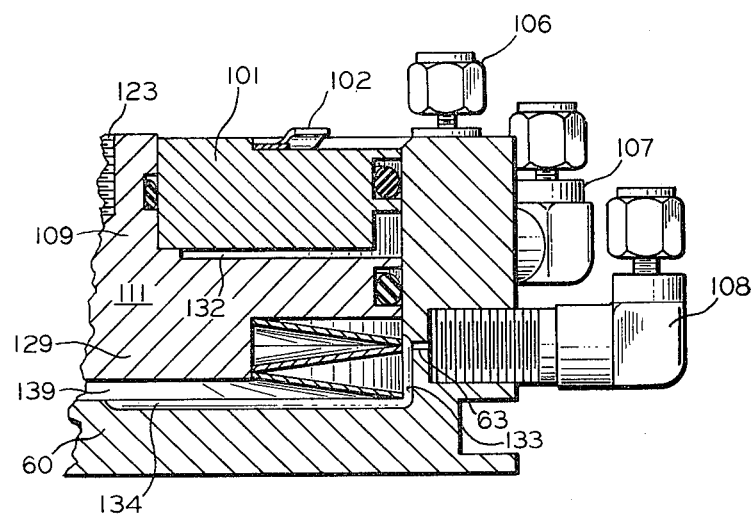
FIG. 7 is a partial cross-sectional view as taken through line 7—7 of FIG. 4.
Figure 8:
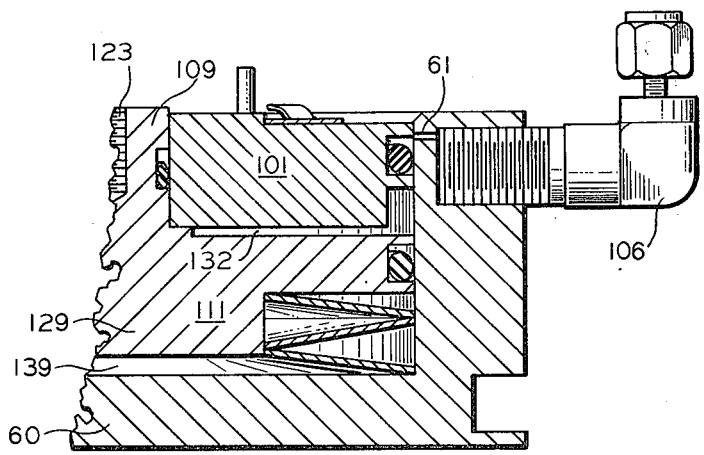
FIG. 8 is a partial cross-sectional view as taken through line 8—8 of FIG. 4.

Spring 102 is located in a chamber 138 defined by the bottom of plunger housing 55 and piston 101. Passage 61 provides communication between chamber 138 and fitting 106. See FIG. 8. A chamber 132 is defined by the bottom of piston 101 and the top of piston 111. Passage 62 provides for communication between chamber 132 and fitting 107. A third chamber 139 is defined by the bottom of piston 111 and the upper inner surface of the base of the piston housing 60. Passage 63 provides for communication between chamber 139 and fitting 108. See FIG. 7. In the internal sidewall of the piston housing 60, there is a groove 133 in chamber 139 extending from the bottom to a point above which the uppermost Bellerville washer contacts the inner sidewall of the piston housing 60. Passage 63 opens into groove 133. Another groove 134 extends from the base of groove 133 along the upper inner surface of the base for piston housing 60 to a point beneath the projection 129 of piston 111.

In the "at rest" position, the Belleville washers force pistons 111 and 101 upward to compress spring 102. With the pistons so positioned, the high portions of projection 109 push plungers 84, 86, and 88 upward so as to force the overlying portions of the diaphragm against the bottom of cap 41. The pressure of the sample and carrier fluids drives rods 85, 87, and 89 downward into recesses 119 to 121 so that they do not cause blockage of flow from the respective two adjacent conduits of conduits 27, 28, 31, 33, 42, and 43.

In the mode of operation described with reference to FIG. 1 during the at rest position, pressure in chamber 132 is evacuated through line 23 which is connected to fitting 107. Pressure is also evacuated from chamber 138 through line 40 which is connected to fitting 106. Actuating fluid, for example air, is passed through line 20, valve 21, line 24, fitting 108 into chamber 139 to assist the washers in maintaining the plungers upward in counteraction to the pressures of the sample and carrier fluid.

At this time, carrier gas flowing continuously in conduit 27, under greater than ambient pressure, enters valve 22 via passage 48, passing downwardly to lower face of cap 41. Since plungers 84 and 88 are up and plunger 89 is down, the carrier fluid forces a flow path extending from recess 96 over plunger 89 to recess 95 and into passage 53 and out of valve 22 via conduit 28 to a column 29. Concurrently sample fluid continuously flowing from sample source conduit 31, under greater than ambient pressure, enters valve 22 through spaced passage 50. Since plungers 86 and 84 are up and plunger 85 is down, the sample fluid forces a flow path extending from recess 92 over plunger 85 to recess 91 and into passage 49, and out of valve 22 via conduit 42, into sample loop 32. Sample fluid re-enters valve 22 from loop 32 via conduit 43 and passage 52. Since plungers 88 and 86 are up and 87 is down, the sample fluid forces a flow path extending from recess 94 over plunger 87 to recess 93 and into spaced passage 51, and out of valve 22, via conduit 33 to sample exhaust.

Upon a signal from the programmer, the valve is switched from its "at rest" position to its "activated" position. The switching is conducted by passing a activating gas through line 20, valve 21, line 23 to piston chamber 132. Pressure is also evacuated from chamber 139 through line 24, valve 21, line 26a, and vacuum pump 40a and pressure is evacuated from chamber 138, through line 40 and vacuum pump 40a.

As the actuating gas pressure builds up in chamber 132, it overcomes first the biasing action of spring 102 on piston 101 to force plunger 85, 87, and 89 upward into sealing contact with the adjacent portions of cushion 83 and diaphragm 76, causing the latter to seal against the lower face of cap 41, thus shutting off sample and carrier gas flow through valve 22. This sequence is characterized as a "make-seal-before-break-seal" mode of operation, and prevents leakage of fluids from one path of flow to the alternate, as the paths of flow are being alternated.

After sufficient pressure has built up in piston chamber 132, piston 111 will also drop. The dropping of piston 111 allows plungers 84, 86, and 88 to retract while plungers 85, 87, and 89 remain in the raised position. Carrier gas from conduit 27 entering valve 22 via passage 48 passes downwardly to the lower face of cap 21. Since plungers 87 and 88 are in sealing contact with the diaphragm, the carrier gas flows from recess 96 across the top of plunger 88 to recess 94 and into spaced passage 52 and thence to the sample loop driving the sample slug trapped therein before it. The carrier gas, with sample fluid entrained, re-enters the valve 22 from loop 32 via conduit 42 and spaced passage 49. Since plungers 85 and 89 are in sealing contact with the diaphragm, the fluid from conduit 43 flows from recess 94 across the top of plunger 84 to recess 95 and into spaced passage 53, and out via conduit 28 to sorption column 29 for separation of the constituents in the sample slug in said column.

Simultaneously, sample fluid still enters valve 22 through passage 50. Since plungers 85 and 87 are in sealing contact with the diaphragm, sample fluid flows from recess 92 over plunger 86 to recess 93 and into passage 51 and out of valve 22 via conduit 33 to sample exhaust.

When pilot valve 21 switches back to the non-excited position, power gas is exhausted from middle chamber 132 by line 23, valve 21 and line 26. At the same time, power gas is supplied to the bottom chamber 139 and the power pistons returned to their initially described "at rest" position in reverse sequence.

The grooves 133 and 134 provide a fluid passageway to passageway 63 so as to minimize the tendency for the Belleville washers 131 to form a seal between themselves and other surfaces with which they are in contact. Thus grooves 133 and 134 result in a more quickly responsive valve than one not having such grooves.

Figure 9:
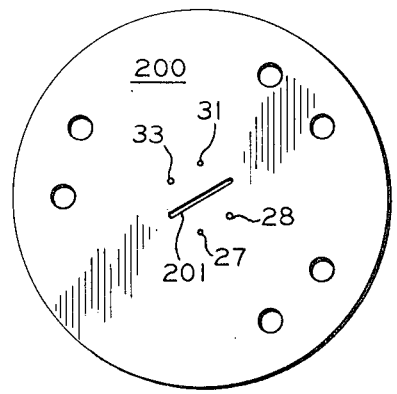
FIG. 9 is a bottom plan view of alternate type of upper member that can be employed in the instant inventive valve.

In FIG. 9 there is shown the bottom of a cap 200 that can be substituted for the cap 41 employed in the inventive valve illustrated in FIGS. 2 through 8. In cap 200, there are only four passageways, those corresponding to passageway 52 and 49 of cap 41 being omitted. A curved groove 201 extends across the lower face of cap 200. The groove 201 results in an internal sample loop. The method of operation and advantages of such a cap are well known to those skilled in this area and are described in the aforementioned U.S. Pat. No. 3,140,615.

It is to be noted that the above given description regarding how the inventive valve can be used is just one of the ways in which it can be satisfactorily employed. When the sample fluid pressures are low enough passages 61 and 64 can be simply used as vents rather than being connected to vacuum and or actuating gas lines as above described. The valve thus is suitable for operation at either high or low pressures regardless of the sample or carrier gas stream pressures.

Also those skilled in the art will readily recognize that the valve can be used as a column switching valve rather than as a sampling valve.

Reasonable variation and modifications are possible within the scope of the foregoing disclosure, the drawings, and the claims to the invention without departing from the spirit thereof.

What is claimed is:

1. A multi-port diaphragm-sealed valve comprising:
a piston housing comprising a tubular sidewall and a base portion closing off the lower end of said tubular sidewall portion;
a plunger housing in sealing engagement with said piston housing to close off the upper end of said tubular sidewall, said plunger housing having upper and lower planar faces, a plurality of spaced-apart passageways therein communicating between the upper and the lower faces of said plunger housing, and a plurality of recesses on the upper face of said plunger housing each extending from one of the passageways in said plunger housing to another of the passageways in said plunger housing;
a cap in sealing engagement with the upper face of said plunger housing and covering the passageways in said plunger housing, said cap having upper and lower planar faces and a plurality of spaced-apart passageways therein communicating between the upper and lower faces of said cap, each said passageway being adapted to be positioned above a different one of the recesses in said plunger housing;

a diaphragm positioned between the lower face of said cap and the upper face of said plunger housing, said diaphragm being adapted to cover the recesses in the upper surface of said plunger housing;

a plurality of plunger means each being positioned in and extending through a respective one of the passageways in said plunger housing;

a first piston means having an opening therethrough, said first piston means being positioned in said piston housing between the base thereof and the lower surface of the plunger housing for reciprocal movement along the central axis of said piston housing in sealing engagement with the inner surface of said tubular sidewall, the upper surface of said first piston having such configurtion that a first chamber is formed between the outer portions thereof and the lower surface of said plunger housing;

a second piston means positioned in said piston housing between the base thereof and the lower surface of said first piston means for reciprocal movement along the central axis of said piston housing in sealing engagement with the inner surface of said tubular sidewall, said second piston means having projecting portion which extends upwardly from the main portion of said second piston through said opening in said first piston means and in sealing. engagement therewith for reciprocal movement therein relative to said first piston means, said first and second piston means being of such configuration that when said pistons are brought into abutting relationship, there is a gap between the outer portions of the lower face of said first piston and the outer portions of the upper face of said second piston, said gap defining a second chamber;

first spring means positioned in said first chamber between the lower face of said plunger housing and the upper face of said first piston means to urge said first piston means away from said lower face of said plunger housing;

second spring means positioned in a third chamber defined by the lower face of said second piston means and the base portion of said piston housing to urge said second piston means toward said plunger housing, said second spring means extending from the inner surface of the tubular sidewall to an opening extending through said second spring means;

a stop means extending downwardly from the lower surface of said second piston and through the opening extending through said second spring means, said stop means extending downwardly a distance sufficient to limit the downward movement of said piston;

a first passageway extending through the tubular sidewall of said piston housing and into communication with said first chamber;

a second passageway extending through the tubular sidewall of said piston housing and into communication with said second chamber;

a third passageway extending through the tubular sidewall and into communication with said third chamber;

a groove in the inner surface of the tubular sidewall of said piston housing in communication with said third passageway and extending in said third chamber from the upper surface of the base portion to a point above that where the uppermost portion of said second spring means contacts said tubular sidewall;

a groove in the upper surface of the base portion of said piston housing extending from the groove in the tubular sidewall to a point beneath said stop means;

wherein the lengths of said plunger means and the configurations of said first and second piston means are such that when said second piston means is in its uppermost position and said first piston is in its lowermost position only a first set of said plunger means engages said diaphragm to seal the corresponding spaces between adjacent pairs of recesses, and when said first and second piston means are in their uppermost positions all of said plunger means engage said diaphragm to seal the corresponding spaces between adjacent pairs of recesses, and when said second piston means is in its lowermost position and said first piston is in its uppermost position only a second set of said plunger means engages said diaphragm to seal the corresponding spaces between said adjacent pairs of recesses;

means for releasably securing said cap to said plunger housing; and means for releasably securing said plunger housing to said piston housing.

2. A valve according to claim 1 wherein the surface area of said diaphragm is about twice as large as necessary to cover the recesses in the upper surface of said plunger housing.

3. A valve according to claim 1 wherein a cushion is positioned between said diaphragm and said recesses on the upper face of said plunger housing, said cushion having dimensions such that it covers all of said plunger housing that underlies said diaphragm.

4. A valve accordisng to claim 3 wherein the surfaces of the diaphragm and the cushion are coextensive and the upper face of said plunger housing includes at least three spaced apart guide pins and the lower face of said cap has openings adapted to receive said guide pins such that said cap and said plunger housing will be in proper alignment, said guide pins being so spaced apart that the outer edges of said diaphragm and said cushion touch the innermost portions of said guide pins.

5. A valve according to claim 4 wherein said first piston means has a first guide pin extending from the lower face thereof and the upper face of said second piston means has an opening adapted to receive said guide pin wherein said opening is so placed as to assure that said first and second piston means are so positioned relative to each other so as is able to properly actuate said plungers, and wherein said first piston means has a second guide pin extending from the upper face thereof and the lower face of the plunger housing has at least one opening adapted to receive said second guide pin wherein each said opening is so positioned as to assure that said first and second pistons will be so positioned relative to said plunger housing so as to be able to properly actuate said plungers.

6. A valve according to claim 5 wherein the upwardly projecting portion of said second piston has a threaded recess in the upper surface thereof into which a threaded device can be secured for assisting in removing said first and second piston means from said piston housing.

7. A valve according to claim 5 wherein said second spring means comprises a plurality of alternately stacked Belleville washers.

8. A valve according to claim 5 wherein said plunger housing includes only six passageways and six plungers arranged in a circular locus with curved recesses extending between said passageways.

9. A valve according to claim 8 wherein said cap includes only six passageways.

10. A valve according to claim 9 wherein said second spring means comprises a plurality of alternately stacked Belleville washers.

11. A valve according to claim 10 wherein the inner surface of said tubular sidewall is cylindrical and said first and second piston means are annular.

12. A valve according to claim 11 wherein said tubular sidewall and said base of said piston housing are one integral piece.

13. A valve according to claim 11 wherein the surface area of said diaphragm is about twice as large as necessary to cover the recesses in the upper surface of said piston housing.

14. A valve according to claim 11 wherein the upwardly projecting portion of said second piston has a threaded recess in the upper surface thereof into which a threaded device can be secured for assisting in removing said first and second piston means from said piston housing.

15. A valve according to claim 1 wherein the upwardly projecting portion of said second piston has a threaded recess in the upper surface thereof into which a threaded device can be secured for assisting in removing said first and second piston means from said piston housing.

16. A valve according to claim 10 wherein said first spring means is weaker than said second spring means.

* * * * *